United States Patent [19]

Pollet et al.

[11] 4,307,175
[45] Dec. 22, 1981

[54] PHOTOGRAPHIC SILVER HALIDE EMULSION MATERIAL CONTAINING AN ANTIFOGGANT PRECURSOR

[75] Inventors: Robert J. Pollet, Vremde; Hendrik E. Kokelenberg, Merksem; Antoon L. Vandenberghe, Hove, all of Belgium

[73] Assignee: AGFA-GEVAERT, N.V., Mortsel, Belgium

[21] Appl. No.: 185,932

[22] Filed: Sep. 10, 1980

[30] Foreign Application Priority Data

Sep. 28, 1979 [GB] United Kingdom ............... 33731/79

[51] Int. Cl.³ ............................................. G03C 1/34
[52] U.S. Cl. .................................... 430/219; 430/611; 430/551
[58] Field of Search ........................ 430/611, 219, 551

[56] References Cited

U.S. PATENT DOCUMENTS 2,939,789 6/1960 Dersch et al. ..................... 430/446
3,140,178 7/1964 Herz et al. ......................... 430/611
3,888,677 6/1975 Abele et al. ........................ 430/611
4,009,029 2/1977 Hammond et al. ................ 430/219

Primary Examiner—Won H. Louie, Jr.
Attorney, Agent, or Firm—A. W. Breiner

[57] ABSTRACT

A photographic material comprising in at least one light-sensitive silver halide emulsion layer and/or in a hydrophilic colloid layer in water-permeable relationship with such an emulsion layer an antifoggant precursor corresponding to one of the following general formulae:

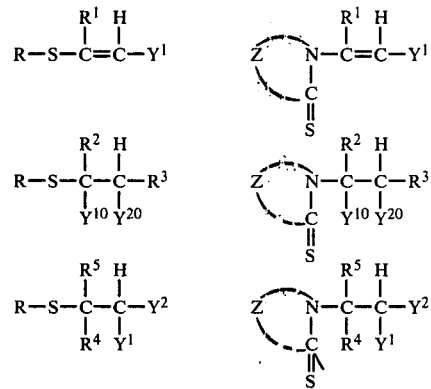

wherein:
each of $Y^1$ and $Y^2$ (same or different) is an acyl group
each of $Y^{10}$ and $Y^{20}$ (same or different) is an aromatic acyl group,
R is an alkyl group, an aryl group or a heterocyclic nitrogen-containing 5-, 6- or 7-membered ring,
$R^1$ is hydrogen, an alkyl group, an aryl group, a carboxyl group in free acid, salt or esterified form, a carbamoyl group or a N-substitued carbamoyl group,
$R^2$ is hydrogen, an alkyl group or an aryl group,
$R^3$ has the same meaning as $Y^{10}$, or is hydrogen, or is an alkyl group or an aryl group, or is a $R^7$-S- group wherein $R^7$ is an alkyl group, an aryl group, or a heterocyclic group,
$R^4$ is hydrogen, an aryl group or a heterocyclic group,
$R^5$ is hydrogen, an alkyl group, an aryl group or a heterocyclic group, and
Z represents the necessary atoms to close a heterocyclic nitrogen-containing 5-, 6- or 7-membered ring.

6 Claims, No Drawings

PHOTOGRAPHIC SILVER HALIDE EMULSION MATERIAL CONTAINING AN ANTIFOGGANT PRECURSOR

This invention relates to silver halide photography and more particularly to silver halide photographic materials containing an antifoggant precursor compound.

It is well known that light-sensitive silver halide materials comprising gelatin silver halide emulsion layers are subject to fog production. Fog appears as a uniform deposit of silver on development and is dependent on a whole series of circumstances and factors, e.g. on the nature of the emulsions, their age, the conditions under which they have been stored and the development conditions.

For particular development conditions the fog tends to be higher when the time of storage and/or the temperature and relative humidity of the atmosphere in which the emulsions are stored are increased. Fog also increases with the degree of development and by development at higher pH and elevated temperatures.

A large variety of compounds have been described in the prior art for reducing fog formation in light-sensitive silver halide emulsions. These compounds can be used more or less successfully dependent on many circumstances, e.g. the type and composition of emulsion in which they are used and the processing conditions of the exposed emulsions, e.g. normal or higher pH and normal or elevated temperatures.

According to a known practice compounds with protected mercapto group are used as described, e.g. in the U.S. Pat. Nos. 2,939,789 and 3,888,677.

In the first mentioned U.S. Patent fog reduction in photographic silver halide emulsions proceeds with azolyl mercaptoalkane diones prepared by allowing to react a 2-mercapto-substituted azole of the imidazole, benzimidazole, oxazole, benzoxazole, selenazole, benzoselenazole, thiazole and benzothiazole series with a halogenated alkylene dicarboxylic compound in which the halogen is attached to a carbon atom adjacent to one carbonyl group and not more than one carbon atom remote from the other. The alkane dione group is represented by the structural formula

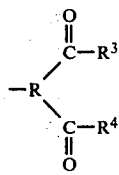

wherein

R is a lower alkylene group of less than three carbon atoms, $R^3$ is an alkyl group or an alkoxy group, and $R^4$ is an alkyl or an alkoxy group having the same values as given for $R^3$.

The second mentioned U.S. Patent relates to silver halide photographic material containing an antifogging agent having the formula:

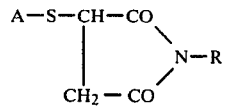

wherein:

A is a nitrogen-containing heterocyclic radical or a 4-acetaminophenyl radical,

R is hydrogen, alkyl of 1 to 4 carbon atoms, aryl or

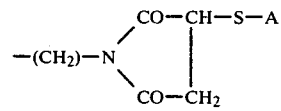

and n is 2 to 4.

The inactivated mercapto group of the latter anti-fogging agent is set free in the alkaline pH medium of the development so that therewith in the photographic material overdevelopment fog can be reduced.

In the U.S. Pat. No. 4,009,029 particular cyanoethyl-containing blocked development restrainers are described that are also called "development-restrainer precursors". They still permit the necessary development to occur before functioning in their role as development restrainers or development arrestors. The precursors contain in their structure a heterocyclic nitrogen-containing 5- or 6-membered ring carrying a sulphur atom linked to a cyanoalkyl group that by hydrolysis of the precursor compound is separated from the remainder of the molecule leaving a heterocyclic mercapto or mercaptide compound acting as antifoggant and development restrainer.

Photographic silver halide emulsion elements containing a precursor convertible to an antifoggant are designed to provide timely release of a development restrainer when the photographic element is processed with an alkaline processing composition. Such photographic elements are especially useful in image-transfer film units where the blocked development restrainers (i.e. the precursors) will permit initial development to occur and will substantially restrain further development upon cleavage.

There is still a need for novel types of fog inhibitors, more particularly for such compounds that effectively block the formation of fog without reducing photographic speed at the same time.

The present invention is based on the discovery of the efficacy of various compounds, hereafter defined, as antifoggant precursors. These compounds have a favourable antifogging action without substantially reducing the photosensitivity of a silver halide emulsion material and they can be activated in a wide range of pH-values.

According to the present invention there is provided a photographic material which comprises a support and at least one silver halide emulsion layer and wherein there is at least one antifoggant precursor in the said emulsion layer and/or in a hydrophilic colloid layer in water-permeable relationship with such an emulsion layer, characterized in that there is at least one said precursor which corresponds to one of the following general formulae

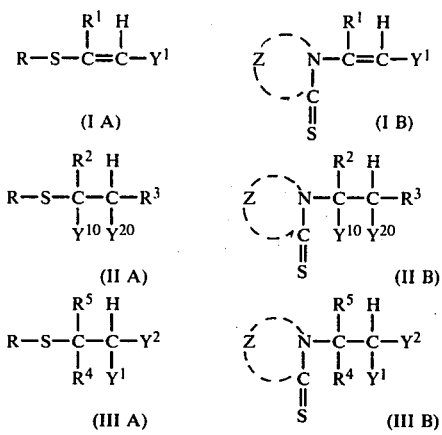

wherein:
each of $Y^1$ and $Y^2$ which may be the same or different, is an acyl group including a substituted acyl group (examples of acyl groups are acyl groups derived from aliphatic or aromatic carboxylic or sulphonic acids, with acyl groups may be substituted, e.g. with halogen)

each of $Y^{10}$ and $Y^{20}$ (which may be the same or different) is an aromatic acyl group including a substituted aromatic acyl group, R is an alkyl or aryl group including said groups in substituted form or in a heterocyclic nitrogen-containing 5-, 6- or 7-membered ring, including said ring in substituted form, $R^1$ is hydrogen, an alkyl or aryl group including said groups in substituted form e.g. phenyl, a carboxyl group in free acid, salt or esterified form, or a carbamoyl or N-substituted carbamoyl group, e.g. N-phenyl-carbamoyl, $R^2$ is hydrogen, or an alkyl or aryl group including said groups in substituted form, e.g. phenyl, $R^3$ has the same meaning as $Y^{10}$ but need not to be identical therewith or is hydrogen or is an alkyl or aryl group including said groups in substituted form or is a $R^7$-S-group wherein $R^7$ is an alkyl group including said group in substituted form (e.g. an hydroxyalkyl group), an aryl group including said group in substituted form or an heterocyclic group including said group in substituted form, $R^4$ is hydrogen, an aryl group including said group in substituted form, e.g. phenyl or an heterocyclic group including said group in substituted form, e.g. a furyl group, $R^5$ is hydrogen or an alkyl, aryl or heterocyclic group including said groups in substituted form, and Z represents the necessary atoms to close a nitrogen-containing 5-, 6- or 7-membered heterocyclic ring including said ring in substituted form.

Examples of heterocyclic rings which may constitute R or be completed by Z are rings derived from triazoles (e.g. 1,2,4-triazoles) and such rings condensed with a benzene ring as in benzotriazoles, tetrazoles, diazoles (e.g. imidazoles, oxadiazoles, thiadiazoles, benzimidazoles), pyrimidines, monoazoles (e.g. oxazoles, benzoxazoles, thiazoles and benzothiazoles), triazines, etc. According to a preferred embodiment an antifoggant precursor containing a 5-(1-phenyl-tetrazolyl) group or a 4-(1-phenyl-tetrazolyl-5-thione) group is used. Such compounds release in alkaline medium the very effective antifoggant 1-phenyl-5-mercaptotetrazole.

The antifoggant precursors in photographic materials used according to the present invention are stable compounds in acid and even neutral medium but in alkaline medium undergo a cleavage yielding a mercapto or mercaptide compound over a large range of pH-values starting from about pH 10. This means that their antifogging activity is not restricted to their use in combination with a particular alkaline developer. Particularly valuable in that respect are the compounds (II A) and (II B) wherein each of $Y^{10}$ and $Y^{20}$ represents a benzoyl group including a substituted benzoyl group.

According to a theory the cleavage reaction may be based on a chemical reaction mechanism known as an elimination reaction. Elimination reactions are those in which two groups are removed from a molecule without being replaced by other groups. In the great majority of such reactions the groups are lost from adjacent carbon atoms, one of the commonly eliminated parts being a proton and the other a nucleophile. The carbon atoms from which the nucleophile, in this case the group

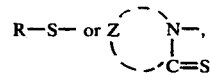

is removed, is referred to as the α-carbon and that loosing a proton as the β-carbon, the overall process being designated as a β-elimination.

Regarding the synthesis of the antifoggant precursors, it is clear for those skilled in the art that where R is a heterocyclic group in addition to isomeric structure A isomeric structure B is obtained. The relative amounts of structures A and B depend on the ratio and reactivity of the automeric structures of the heterocyclic starting compound containing

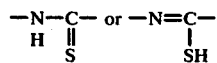

available for reaction with the electrophile (co-reactant). This ratio depends upon e.g. the structure of the electrophile, the solvent and the base used in the addition reaction. In the synthesis, which actually is an addition reaction, hydrogen of the —SH group or of the —NH— group is transferred to a carbon atom of a double or triple carbon bond of the co-reactant.

Co-reactants for the preparation of compounds (I A) and (I B) are substituted acetylenes.

The co-reactant for the preparation of compounds (II A), (II B), (III A) and (III B) can be prepared by one of the following reaction schemes:

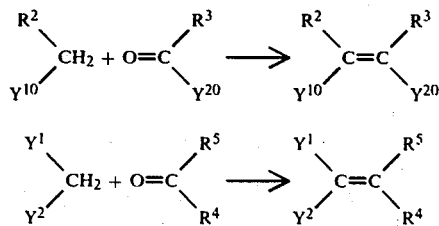

Compounds being within the scope of general formula (I A) are listed in the following table 1 with their melting point.

TABLE 1

R—S—C(R$^1$)=CH—Y$^1$

| No. of compound | R | R$^1$ | Y$^1$ | Melting point °C. |
|---|---|---|---|---|
| 1 | PT | H | SO$_2$C$_6$H$_5$ | 130 |
| 2 | PT | C$_6$H$_5$ | SO$_2$C$_6$H$_5$ | 155 |

PT stands for

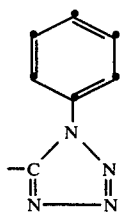

A compound (compound no. 3) falling within the scope of general formula (I B) has the following structural formula:

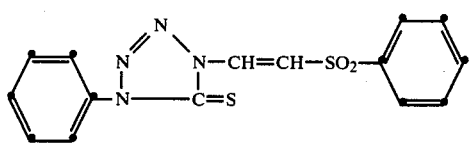

(melting point: 145° C.)

Compounds being within the scope of general formula (II A) are listed in the following table 2 with their melting point.

TABLE 2

R—S—CH(Y$^{10}$)—CH(Y$^{20}$)—R$^3$

| No. of compound | R | Y$^{10}$/Y$^{20}$ | R$^3$ | Melting point °C. |
|---|---|---|---|---|
| 4 | PT | COC$_6$H$_5$ | H | 134 |
| 5 | phenyl | COC$_6$H$_5$ | H | 80 |
| 6 | PT | CO—C$_6$H$_4$—CH$_3$ | H | 153 |
| 7 | PT | CO—C$_6$H$_4$—Cl | H | 132 |
| 8 | PT | CO—C$_6$H$_4$—F | H | 90 |
| 9 | (3,4-dichloro)PT | COC$_6$H$_5$ | H | 152 |

PT has the same meaning as defined at the end of table 1.

Compounds within the scope of general formula (II B) are listed in the following table 3 with their melting point.

TABLE 3

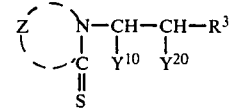

| No. of compound | Y$^{10}$/Y$^{20}$ | R$^3$ | Melting point °C. |
|---|---|---|---|
| 10 | COC$_6$H$_5$ | H | 116 |
| 11 | CO—C$_6$H$_4$—CH$_3$ | H | 146 |
| 12 | CO—C$_6$H$_4$—Cl | H | 146 |
| 13 | CO—C$_6$H$_4$—F | H | 146 |

Z represents the group

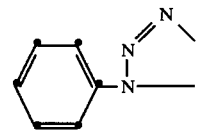

Compounds within the scope of general formula (III A) are listed in the following table 4 with their melting point.

TABLE 4

R—S—CH(R$^4$)—CH(Y$^1$)—Y$^2$

| No. of compound | R | R$^4$ | Y$^1$/Y$^2$ | Melting point °C. |
|---|---|---|---|---|
| 14 | phenyl | H | COC$_6$H$_5$ | 78 |
| 15 | phenyl | phenyl | COCH$_3$ | 119 |
| 16 | phenyl | phenyl | COC$_6$H$_5$ | 142 |
| 17 | phenyl | furyl | COCH$_3$ | 65 |

Compounds within the scope of general formula (III B) are e.g.

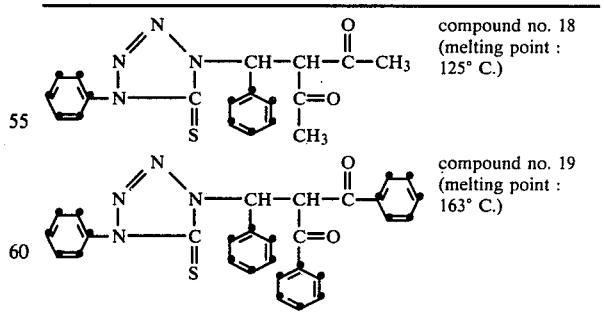

compound no. 18 (melting point: 125° C.)

compound no. 19 (melting point: 163° C.)

Examples of preparation of the above compounds are given to show the procedure of preparation of the blocked antifoggants according to the mentioned general formulae.

PREPARATION 1

Compound 1

Compound 3

20.2 g (0.1 mole) of 1-chloro-2-(phenylsulphonyl)ethylene [Gazz. Chim. Ital. 86, 406 (1956)], dissolved in 75 ml of ethanol were added to a solution of 20 g (0.1 mole) of the sodium salt of 1-phenyl-5-mercaptotetrazole in 125 ml of ethanol and the reaction mixture was boiled with stirring for 4 h.

After cooling the precipitate was sucked off and boiled twice with ethanol. From the hot ethanol filtrates 17 g of reaction product were isolated. Melting point: 132° C. The reaction product compound 1 and its isomer compound 3 were obtained in a 1:1 by weight ratio.

Compound 1 melting at 130° C. and compound 3 melting at 145° C. were separated by chromatography. The structure of said compounds was confirmed by NMR.

PREPARATION 2

Compound 2

0.2 mole of 1-phenyl-5-mercaptotetrazole dissolved in 300 ml of ethyl acetate was dropwise added to a solution of 0.2 mole of 1-phenyl-2-sulphophenyl-acetylene (W. Truce et al, J. Am. Chem. Soc. 78, 2760 (1956)) dissolved in 80 ml of ethyl acetate. After keeping the reaction mixture at room temperature for 24 h the solvents were evaporated and the residue was washed with methylene chloride. Melting point: 155° C. The structure of compound 2 was confirmed by NMR.

PREPARATION 3

Compound 4

47.2 g (0.2 mole) of trans-dibenzoyl-ethylene [Org. Syn. Coll. Vol. I, 71 (1932)] and 35.6 g (0.2 mole) of 1-phenyl-5-mercaptotetrazole were dissolved successively in 200 ml of hot acetic acid and heated at 100° C. for 6 h with stirring. A precipitate was gradually formed.

Yield: 69 g (81%). Melting point: 134° C. The structure of said compound was confirmed by NMR.

Compounds 5 and 9 were prepared analogously but starting from thiophenol and 1-(3,4-dichloro-phenyl)-5-mercaptotetrazole respectively instead of from 1-phenyl-5-mercaptotetrazole.

Compounds 6, 7 and 8 were likewise analogously synthesized but by using the appropriate dibenzoylethylene [J. Conant and R. Lutz, J. Am. Chem. Soc., 45, 1303 (1923)].

PREPARATION 4

Compound 10

47.2 g (0.2 mole) of trans-dibenzoylethylene and 35.6 g (0.2 mole) of 1-phenyl-5-mercaptotetrazole were dissolved in 950 ml of boiling ethanol and boiled with stirring together with 10 ml of a 40% by weight solution in methanol of benzyltrimethylammonium hydroxide for 18 h. The formed precipitate was twice recrystallized from 350 ml of ethanol. Yield: 39 g (47%). Melting point: 116° C. The structure of said compound was confirmed by NMR.

Compounds 11, 12 and 13 were prepared analogously but starting from the appropriate dibenzoylethylenes [J. Conant and R. Lutz, J. Am. Chem. Soc. 45, 1303 (1923)].

PREPARATION 5

Compound 14

16 g (0.2 mole) of formaldehyde (40% by weight aqueous solution) were added dropwise to a solution of 44.8 g (0.2 mole) of dibenzoylmethane, 22 g (0.2 mole) of thiophenol and 6 ml of triethylamine in 350 ml of diethyl ether. The reaction mixture was boiled under nitrogen atmosphere for 8 h, and then concentrated. The oily residue obtained was purified by recrystallizing twice from a hydrocarbon solvent having a boiling range of 88°–105° C. Yield: 19.5 g (28%). Melting point: 78° C. The structure of said compound was confirmed by NMR.

PREPARATION 6

Compound 15

22 g (0.2 mole) of thiophenol were added to a solution of 13.6 g (0.2 mole) of sodium methylate dissolved in 150 ml of ethanol. Thereupon 44.9 g (0.2 mole) of 3-($\alpha$-chlorobenzyl)acetylacetone [Ann. 281, 79 (1894)] dissolved in 600 ml of hot ethanol were added dropwise. A voluminous precipitate was formed and left overnight, sucked off and washed with a mixture of ethanol and water (1:1 by volume). Yield: 46.5 g (77%). Melting point: 119° C. The structure of said compound was confirmed by NMR.

PREPARATION 7

Compounds 16 and 17

Compounds 16 and 17 were prepared by addition reaction of thiophenol in acetic acid at 70° C. with benzaldibenzoylmethane [E. Pratt and E. Werbbe, J. Am. Chem. Soc., 72, 4638 (1950)] and furalacetylacetone respectively. The structure was confirmed by NMR.

PREPARATION 8

Compound 18

37.6 g (0.2 mole) of benzalacetylacetone and 35.6 g (0.2 mole) of 1-phenyl-5-mercaptotetrazole were dissolved successively in 250 ml of acetone. To the solution 2 g of benzyltrimethylammonium fluoride were added and the reaction mixture was refluxed under nitrogen atmosphere for 16 h. The solvent was evaporated and the residue recrystallized from 500 ml of ethanol. Yield: 29 g (40%). Melting point: 125° C. The structure of compound 18 was confirmed by NMR.

Compound 19 was prepared analogously but starting from benzaldibenzoylmethane instead of from benzalacetylacetone.

The photographic material of the present invention comprises a support and at least one light-sensitive silver halide emulsion layer wherein the emulsion layer and/or a hydrophilic colloid layer in water-permeable relationship with the emulsion layer comprises a compound corresponding to one of the general formulae defined hereinbefore.

Antifoggant precursors corresponding to anyone of the above general formulae may be incorporated in various types of light-sensitive silver halide emulsions, e.g. for professional photography such as in X-ray emulsions, and in graphic purpose emulsions and in emulsions intended for so-called amateur photography, in continuous tone or high contrasty emulsions, in silver halide emulsions suited for silver complex diffusion transfer processes, in non-spectrally sensitized emulsions and in spectrally sensitized emulsions. They may be incorporated in high-speed, low-speed, black-and-white and colour emulsions.

According to a special embodiment one or more of said antifoggant precursors is or are used in a photographic material for the production of dye images by image-wise transfer of a dye or dye precursor into a receiving element. The receiving element may be a separate material or the receiving element together with the light-sensitive element makes part of mono-pack material. The precursors are generally useful in dye image-transfer film operating with image-dye-providing materials as mentioned, e.g., in the U.S. Pat. No. 4,009,029, the German Pat. No. 1,095,115, the German Offenlegungsschriften Nos. 1,772,929-2,019,430-2,404,900 and 2,543,902, the Belgian Pat. No. 861,241 and the published European Patent Application No. 0 004 399. The antifoggant precursors are also generally useful in an image-transfer assembly, which comprises:

1. a photosensitive element comprising a first support which carries at least one photo-sensitive layer containing a silver halide emulsion having associated therewith an image-dye-providing substance, and which preferably carries at least three such emulsion layers, these containing a blue-sensitive silver halide emulsion, a green-sensitive silver halide emulsion, and a red-sensitive silver halide emulsion, respectively;

2. an image-receiving layer that is located on a second support and is superposed on said silver halide emulsion layer(s) which is (are) carried by said first support, thereby forming a mono-pack assembly in which the said image-receiving layer is in waterpermeable relationship with said photo-sensitive silver halide emulsion layer(s); and optionally 3. means containing an alkaline processing liquid adapted to discharge its contents between elements 1 and 2.

A mono-pack material incorporating at least one of the above antifoggant precursors and suitable for a dye diffusion transfer process may comprise, e.g. the following constituent layers:

1. a transparent supporting layer,
2. an image-receiving layer,
3. a light-impervious layer,
4. at least one light-sensitive silver halide emulsion layer and at least one non-diffusible image-dye-providing substance associated with such layer(s)
5. a retarding layer,
6. an acid polymer layer, and
7. a transparent cover layer.

The mono-pack material can be formed by combining two separately fabricated parts viz. a light-sensitive part (comprising layers 1 to 4) on the one hand and a cover part (comprising layers 5 to 7) on the other hand, these two parts being then placed together with their active surfaces in contact and laminated together at the edges, optionally with the interposition of spacer strips so that a space is left for an accurately calculated quantity of the alkaline processing liquid.

The layers 5 and 6, which together form the neutralisation system, may alternatively be arranged between the supporting layer (1) and the image-receiving layer (2) but in the reverse sequence so that the polymer layer (6) is next to the supporting layer (1). Another practical arrangement is to provide acid polymer and retarding layers at both such positions in the pack.

Means may be provided for introducing the alkaline processing liquid between the light-sensitive part and the cover part as above referred to e.g. in the form of a breakable container arranged at the longitudinal edges of the material so that it pours out its contents between two adjacent layers of the mono-pack material when subjected to mechanical forces. More details with respect to composition suitable for the above layers can be found in Belgian Pat. No. 861,241. The pH of the alkaline processing liquids of mono-pack material is usually fairly high i.e. about 11.5 and may be between 13 and 14.

In the photographic silver halide emulsions the antifoggant precursors may be admixed with various light-sensitive silver salts, e.g. silver bromide, silver iodide, silver chloride, or mixed silver halides, e.g. silver chlorobromide, silver bromoiodide, or silver chlorobromoiodide.

The silver halides can be dispersed in the common hydrophilic colloids such as gelatin, casein, zein, polyvinyl alcohol, carboxymethylcellulose, alginic acid, etc., gelatin being, however, favoured.

The amount of antifoggant precursor for use according to the present invention in the light-sensitive silver halide material may vary between wide limits and depends on each individual compound and material employed. Optimum amounts can be determined easily by routine experiments. Generally the amount varies from about 0.001 to about 20 millimoles, preferably from about 0.01 to about 5 millimoles per mole of silver halide. The way in which the antifoggant precursors are added to the silver halide emulsions is not critical and the addition may proceed at any stage in the emulsion preparation; they can be added before, during or after addition to the emulsion of spectral sensitizers. They are preferably added just before coating of the emulsion on a suitable support such as e.g. paper, glass, film or metal-laminated paper.

Instead of incorporating the antifoggant-precursors into the emulsion layer they can also be incorporated into another water-permeable colloid layer of the photographic material, e.g. a gelatin protective top-layer or intermediate layer, which is in water-permeable relationship with said emulsion layer.

The silver halide emulsions containing in accordance with the present invention an antifoggant precursor or mixture thereof may be chemically sensitized by effecting the ripening in the presence of small amounts of sulphur-containing compounds such as allyl thiocyanate, allyl thiourea, sodium thiosulphate, etc. The emulsions may also be chemically sensitized by means of reductors e.g. tin compounds as described in U.K. Pat. No. 789,823, and small amounts of noble metal compounds such as gold, platinum, palladium, iridium, ruthenium and rhodium compounds as described by R. Koslowsky, Z. Wiss. Photogr. Photophys. Photochem., 46, 65-72 (1951).

The emulsions may be spectrally sensitized or not. It is advantageous to sensitize them spectrally according to methods well known in the art to make them orthosensitized or panchromatically sensitized. Spectral sensitizers that can be used are, e.g., the cyanines, merocyanines, complex (trinuclear) cyanines, complex (trinuclear) merocyanines, styryl dyes, oxonol dyes and the like. Suchlike spectrally sensitizing dyes have been described by F. M. Hamer in "The Cyanine Dyes and Related Compounds" (1954).

The emulsions may be hardened in the conventional way, e.g. by means of formaldehyde, halogen-substituted aldehydes e.g. mucochloric acid and mucobromic acid, glutaraldehyde, diketones, dioxan derivatives, aziridine, oxypolysaccharides, methansulphonic acid esters, vinylsulphone compounds or hydroxydichlorotriazine.

Other conventional addenda may be added to the emulsions, e.g. plasticizers, coating aids, hardneing agents, anti-staining agents, matting agents, developing agents, wetting agents, colour couplers, compounds that sensitize the emulsions by development acceleration, other fog-inhibitors and emulsion-stabilizing agents, etc.

Compounds that sensitize the emulsions by development acceleration are, e.g., alkylene oxide polymers. These alkylene oxide polymers may be of various type, e.g. polyethylene glycol having a molecular weight of 1500 or more, alkylene oxide condensation products or polymers as described among others in U.S. Pat. Nos. 1,970,578—2,240,472—2,423,549—2,441,389—2,531,832 and 2,533,990, in U.K. Pat. Nos. 920,637—940,051—945,340—991,608 and 1,015,023 and in Belgian Pat. No. 648,710 or polythioethers. Other compounds that sensitize the emulsion by development acceleration and that may be used in combination with the foregoing polymeric compounds are quaternary ammonium and phosphonium compounds and ternary sulphonium compounds as well as onium derivatives of amino-N-oxides as described in U.K. Pat. No. 1,121,696.

The silver halide emulsions and the processing solutions may also comprise common antifoggants and emulsion stabilizers e.g. homopolar or salt-like compounds of mercury with aromatic and heterocyclic rings (e.g. mercaptotriazoles) simple mercury compounds, mercury sulphonium double salts and other mercury compounds of the kind described in Belgian Pat. Nos. 524,121—677,337—707,386 and 709,195, pyrimidine derivatives as described in German Auslegeschrift No. 1,294,188, aminothiazole derivatives combined with derivatives of azaindenes as described in German Auslegeschrift No. 1,209,426. Other suitable emulsion stabilizers are the azaindenes, particularly the tetra- or pentaazaindenes and especially those substituted by hydroxy- or amino groups. Suchlike compounds have been described by Birr in Z. Wiss. Photogr. Photophys. Photochem. 47, 2–58 (1952). The emulsions may further comprise as stabilizers heterocyclic nitrogen-containing mercapto compounds such as benzothiazoline-2-thione and 1-phenyl-5-mercapto-tetrazole, which may comprise sulpho or carboxyl groups, mercaptocarboxylic derivatives of disulphides as described in U.S. Pat. No. 1,742,042 or derivatives of, e.g. heterocyclic mercapto compounds, nitrobenzene compounds as described in U.K. Pat. No. 1,399,449, disulphides, sulphinic acids such as benzene sulphinic acid and toluene sulphinic acid, thiosulphinic or thiosulphonic acids such as benzenethiosulphinic acid, toluenethiosulphonic acid, p-chloro-benzenethiosulphonic acid sodium salt, propylthiosulphonic acid potassium salt, butylthiosulphonic acid potassium salt, etc.

Processing of photographic materials containing one or more of the above antifoggant precursors may occur at room temperature or at elevated temperature, e.g. above 30° C.

In order to demonstrate the pH dependency of cleavage of representative antifoggant precursors according to one of the above general formulae in comparison with some prior art compounds the degree of cleavage expressed in mole percent was measured at different pH-values and recorded in the following table 5.

TABLE 5

| No. of com-pound | Cleavage degree in mole % | | | | |
|---|---|---|---|---|---|
| | pH = 4.2 | pH = 7.0 | pH = 10.0 | pH = 11.5 | pH = 12.7 |
| 5 | 0 | 0 | 0 | 7 | 25 |
| 7 | 0 | 2 | 10 | 100 | 100 |
| 11 | 0 | 0 | 0 | 59 | 90 |
| 12 | 0 | 0 | 12 | 100 | 100 |
| 14 | 0 | 0 | 10 | 55 | 100 |
| 15 | 0 | 0 | 80 | 80 | 100 |
| 18 | 0 | 5 | 80 | 100 | 100 |
| X | 0 | 0 | 65 | — | 57 |
| Y | 0 | 0 | 8 | 100 | 100 |
| Q | 100 | 100 | 100 | 100 | 100 |

The compounds X, Y and Q have respectively the following structural formulae:

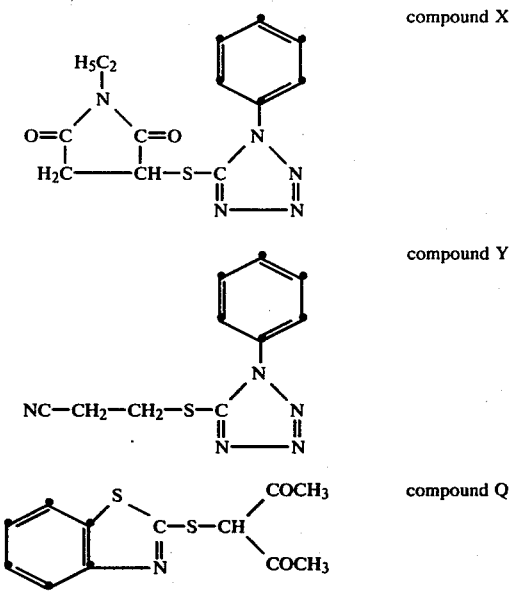

and are described in the U.S. Pat. Spec. Nos. 3,888,677, 4,009,029 and 2,939,789 respectively.

In order to determine said degree of cleavage 2 mmole of the mentioned compound were dissolved in 10 ml of tricresyl phosphate and 1 ml of a 10% by weight aqueous solution of HOSTAPON T (trade name) added thereto. The obtained solution was diluted to a volume of 100 ml by adding a 5% by weight aqueous solution of gelatin whilst vigorously stirring. From the mixture 25 ml were taken and added to 25 ml of a buffer solution having the indicated pH. After keeping the samples at 35° C. for 4 h the content of mercapto compound was potentiometrically titrated with a 0.1 N aqueous silver nitrate solution and from the result the degree of cleavage was calculated. The samples at pH 11.5 and 12.7 were acidified with acetic acid up to a pH 4 before titration.

(HOSTAPON T is a registered trade name for oleyl-N-methyltauride sodium salt of Farbwerke Hoechst A.G., W. Germany).

The following examples illustrate the fog-inhibiting action of compounds corresponding to one of the general formulae mentioned hereinbefore and show their favourable effect on speed and gradation.

EXAMPLE 1

To several series of aliquot portions of a photographic ammoniacal silver bromoiodide gelatin emulsion (6 mole % of iodide) comprising per kg an amount of silver halide equivalent to 50 g of silver nitrate, one of the antifoggant precursors of table 6 hereinafter was added in a concentration expressed in mmole per kg of silver halide emulsion. The emulsion portions were coated on a conventional support and dried.

The sensitometric values obtained after exposure through a step wedge of constant 0.15 and processing of a strip of the freshly prepared materials and of a strip of the incubated materials that were stored at 57° C. and 34% relative humidity for 5 days are listed in table 6.

The values given for the speed are relative values corresponding to density (D) 0.1 above fog; the speed of the fresh materials (controls) comprising no antifoggant precursor is given the value 100. The speed values of the strips containing the antifoggant precursors are percental values in respect of these controls. The density (D) values given for the fog are absolute values. The value given for $\gamma$ is the value of gradation derived from the characteristic curve over an exposure range of log E=0.60 starting from a density value of 0.5 above fog.

Develoment occurred at 20° C. for 5 min in a developing solution having the following composition:

| water | 800 ml |
| --- | --- |
| p-monomethylaminophenol sulphate | 1.5 g |
| anhydrous sodium sulphite | 50 g |
| hydroquinone | 6 g |
| anhydrous sodium carbonate | 32 g |
| potassium bromide | 2 g |
| water to make | 1000 ml |
| | (pH = 10.5) |

TABLE 6

| Compound/ kg silver halide emulsion | Fresh material | | | Incubated material | | |
| --- | --- | --- | --- | --- | --- | --- |
| | fog | speed | $\gamma$ | fog | speed | $\gamma$ |
| control 1 | 0.16 | 100 | 2.05 | 1.43 | 59 | 0.90 |
| compound 2 1 mmole | 0.10 | 87 | 1.90 | 0.93 | 96 | 1.10 |
| control 2 | 0.08 | 100 | 2.00 | 0.54 | 168 | 1.45 |
| compound 10 1 mmole | 0.10 | 107 | 1.90 | 0.24 | 151 | 1.73 |
| control 3 | 0.11 | 100 | 1.40 | 1.68 | — | — |
| compound 15 0.5 mmole | 0.08 | 66 | 1.80 | 0.36 | 100 | 1.02 |
| 1 mmole | 0.09 | 66 | 1.75 | 0.23 | 97 | 1.35 |
| control 4 | 0.10 | 100 | 1.42 | 0.99 | 78 | 0.82 |
| compound 18 0.05 mmole | 0.07 | 71 | 1.50 | 0.21 | 127 | 1.10 |
| 0.1 mmole | 0.06 | 68 | 1.42 | 0.11 | 90 | 0.92 |
| control 5 | 0.15 | 100 | 1.40 | 0.62 | 141 | 1.26 |
| compound Y 0.5 mmole | 0.16 | 97 | 1.38 | 0.66 | 123 | 1.24 |

Compound Y has the structural formula already given before.

Missing results (indicated by a dash) in the table 6 as well as in the following tables 7 and 8 point to the fact that measurement was not possible because of too high fog values.

EXAMPLE 2

To several series of aliquot portions of a photographic ammoniacal silver bromoiodide gelatin emulsion (2 mole % of iodide) comprising per kg an amount of silver halide equivalent to 180 g of silver nitrate, one of the antifoggant precursors of table 7 hereinafter was added in a concentration expressed in mmole per kg of silver halide emulsion. The emulsion portions were coated on a conventional support and dried.

The sensitometric values obtained after exposure through a step wedge of constant 0.15 and processing of a strip of the freshly prepared materials and of a strip of the incubated materials that were stored at 57° C. and 34% relative humidity for 5 days are listed in table 7.

The values given for the speed are relative values corresponding to density (D) 1 above fog; the speed of the fresh materials comprising no antifoggant precursor (controls) is given the value 100. The speed values of the strips containing the antifoggant precursors are percental values in respect of these controls. The density (D) values given for the fog are absolute values. The value given for $\gamma$ is the value of gradation derived from the characteristic curve over an exposure range of log E=0.90 starting from a density value of 0.25 above fog.

Development occurred at 20° C. for 4 min in a developing solution having the following composition:

| water | 800 ml |
| --- | --- |
| 1-phenyl-pyrazolidin-3-one | 1 g |
| anhydrous sodium sulphite | 50 g |
| hydroquinone | 18 g |
| anhydrous sodium carbonate | 50 g |
| potassium bromide | 10 g |
| water to make | 1000 ml |
| | (pH = 10.1) |

In the following table 7 the compound Z is the unblocked antifoggant 1-phenyl-5-mercaptotetrazole.

TABLE 7

| Compound kg of silver halide emulsion | Fresh material | | | Incubated material | | |
| --- | --- | --- | --- | --- | --- | --- |
| | fog | speed | $\gamma$ | fog | speed | $\gamma$ |
| control 1 | 0.14 | 100 | 3.15 | 1.96 | — | — |
| compound 10 1 mmole | 0.13 | 93 | 3.90 | 0.20 | 93 | 3.05 |
| control 2 | 0.17 | 100 | 3.00 | 1.50 | — | — |
| compound 2 2.5 mmoles | 0.17 | 69 | 2.76 | 0.51 | 76 | 2.75 |
| control 3 | 0.18 | 100 | 2.62 | 0.67 | 117 | 2.06 |
| compound X 0.2 mmole | 0.18 | 66 | 2.45 | 0.23 | 69 | 2.20 |
| compound Z 0.05 mmole | 0.18 | 69 | 2.65 | 0.21 | 69 | 2.35 |
| 0.1 mmole | 0.18 | 56 | 2.75 | 0.19 | 51 | 2.15 |
| 0.2 mmole | 0.18 | 31 | 1.65 | 0.18 | — | 1.02 |

EXAMPLE 3

To several series of aliquot portions of a photographic ammoniacal silver bromoiodide gelatin emulsion (2 mole % of iodide) comprising per kg an amount of silver halide equivalent to 180 g silver nitrate, one of the antifoggant precursors of table 8 hereinafter was added in a concentration expressed in mmole per kg of silver halide emulsion. The emulsion portions were coated on a conventional support and dried.

The sensitometric values obtained after exposure through a step-wedge of constant 0.15 and processing of a strip of the freshly prepared materials and of a strip of the incubated materials that were stored at 57° C. and 34% relative humidity for 5 days are listed in table 8.

The values given for the speed are relative values corresponding to density (D) 1 above fog; the speed of the fresh materials comprising no antifoggant precursor according to the invention (controls) is given the value 100. The speed values of the strips containing the antifoggant precursors are perecental values in respect of these controls. The density (D) values given for the fog are absolute values. The value given for $\gamma$ is the value of gradation derived from the characteristic curve over an exposure range of log E=0.90 starting from a density value of 0.25 above fog.

Development occurred at 35° C. for 90 s in a developing solution prepared by mixing 1000 ml of solution A with 2800 ml of water, 100 ml of solution B and 100 ml of solution C (pH of the mixture=10.35).

| Composition of solution A | |
|---|---|
| 40% by weight aqueous solution of potassium hydroxide | 165 ml |
| 65% by weight aqueous solution of potassium sulphite | 346 ml |
| hydroquinone | 112 g |
| 1-phenyl-5-mercaptotetrazole | 40 mg |
| anhydrous potassium carbonate | 60 g |
| potassium chloride | 3.4 g |
| diethylene glycol | 10 ml |
| demineralized water to make | 1000 ml |
| Composition to solution B | |
| glacial acetic acid | 45 ml |
| 1-phenyl-pyrazolidin-3-one | 6.2 g |
| ethylene glycol to make | 100 ml |
| Composition to solution C | |
| 25% by weight aqueous solution of glutardialdehyde | 80 ml |
| potassium metabisulphite | 36 g |
| demineralized water to make | 100 ml |

TABLE 8

| Compound per kg of silver halide emulsion | Fresh material | | | Incubated material | | |
|---|---|---|---|---|---|---|
| | fog | speed | $\gamma$ | fog | speed | $\gamma$ |
| control | 0.21 | 100 | 3.11 | 2.75 | — | — |
| compound 10 | | | | | | |
| 0.2 mmole | 0.19 | 63 | 3.96 | 0.60 | 95 | 3.46 |
| 0.5 mmole | 0.18 | 54 | 3.86 | 0.25 | 68 | 3.86 |
| compound Z | | | | | | |
| 0.2 mmole | 0.21 | 37 | 3.91 | 0.25 | 19 | 2.14 |
| control 2 | 0.20 | 100 | 3.86 | 2.82 | — | — |
| compound 2 | | | | | | |
| 2.5 mmoles | 0.19 | 55 | 3.72 | 0.63 | 95 | 3.15 |

EXAMPLE 4

To several series of aliquot portions of a photographic silver chlorobromide gelatin emulsion (27.5 mole % of bromide) comprising a colour coupler for producing a magenta dye and being already stabilized with the usual stabilizer 4-hydroxy-6-methyl-1,3,3a,7-tetrazaindene, one of the antifoggant precursors of table 9 hereinafter was added in a concentration expressed in mmole per kg of silver halide emulsion. The emulsion portions were coated on a conventional support at a coverage of 2.98 g of gelatin per sq.m and an amount of silver halide equivalent with 0.78 g of silver nitrate per sq.m.

The sensitometric values obtained with white light exposure through a continuous grey wedge of constant 0.15 and processing of a strip of the freshly prepared materials and of a strip of the incubated materials that were stored at 57° c. and 34% relative humidity for 5 days are listed in the same table 9.

The values given for the speed are relative values corresponding to density (D) 1.1 above fog; the speed of the fresh material (control) comprising no antifoggant precursor is given the value 100. The speed values of the strips containing the antifoggant precursors are percental values in respect of these controls. The density (D) values given for the fog are absolute values. The value given for $\gamma$ is the value of gradation derived from the characteristic curve over an exposure range of log E=0.45 starting from a density value of 1.1 above fog.

Development occurred at 36.7° C. for 3 min 15 s in a colour developing solution having the following composition:

| 2-amino-5-diethylamino-toluene hydrochloride | 2.95 g |
|---|---|
| anhydrous sodium sulphite | 4.35 g |
| anhydrous sodium carbonate | 17.1 g |
| sodium bromide | 1.72 g |
| water to make | 1000 ml |
| | (pH = 10.53) |

Thereupon the material was treated for 40 s at 27° C. with an aqueous sulphuric acid stop-bath having a pH 0.9 and then rinsed for 40 s in water at a temperature of 18° C.

Fixing of the material proceeded for 40 s at 27° C. in a fixing bath having the following composition:

| sodium thiosulphate | 58 g |
|---|---|
| anhydrous sodium sulphite | 2.5 g |
| sodium hydrogen sulphite | 10.3 g |
| water up to | 1000 ml |
| | (pH = 5.8) |

Thereupon the material was rinsed for 40 s in water at 18° C., and then bleached for 1 min at 27° C. in the following bleaching bath:

| potassium hexacyanoferrate (III) | 30 g |
|---|---|
| sodium bromide | 17 g |
| water up to | 1000 ml |
| | (pH = 6.5) |

Fixing was repeated for 40 s at 27° C. using the already defined fixing bath and finally the material was treated at 18° C. in an aqueous stabilizing bath containing per liter 12 ml of a 40% by weight aqueous solution of formaldehyde and a minor amount of wetting agent.

TABLE 9

| Compound/ kg of silver halide emulsion | Fresh material | | | Incubated material | | |
|---|---|---|---|---|---|---|
| | fog | speed | $\gamma$ | fog | speed | $\gamma$ |
| control | 0.334 | 100 | 2.65 | 0.387 | 117 | 2.67 |
| compound 15 | | | | | | |
| 0.2 mmole | 0.281 | 92 | 2.52 | 0.319 | 102 | 2.55 |
| compound Q | | | | | | |
| 0.2 mmole | 0.317 | 92 | 2.62 | 0.383 | 108 | 2.56 |

We claim:

1. A photographic material which comprises a support and at least one light-sensitive silver halide emulsion layer and wherein there is at least one antifoggant precursor in the said emulsion layer and/or a hydrophilic colloid layer in water-permeable relationship with such an emulsion layer, characterized in that there is at least one said precursor which corresponds to one of the following general formulae (I A), (I B), (II A), (II B), (III A) or (III B):

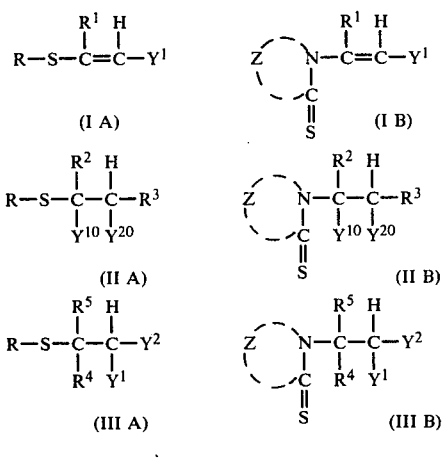

wherein:
each of $Y^1$ and $Y^2$ (same or different) is an acyl group,
each of $Y^{10}$ and $Y^{20}$ (same or different) is an aromatic acyl group,
R is an alkyl group, an aryl group, a heterocyclic nitrogen-containing 5-, 6- or 7-membered ring, $R^1$ is hydrogen, an alkyl group, an aryl group, a carboxyl group in free acid, salt or esterified form, or a carbamoyl group, $R^2$ is hydrogen, an alkyl group or an aryl group, $R^3$ has the same meaning as $Y^{10}$ but need not be identical thereto, or is hydrogen, an alkyl group, an aryl group, or a $R^7$-S- group wherein $R^7$ is an alkyl group, an aryl group, or a heterocyclic group, $R^4$ is hydrogen, an aryl group or a heterocyclic group, $R^5$ is hydrogen, an alkyl group, an aryl group or a heterocyclic group, and Z represents the necessary atoms to close a nitrogen-containing 5-, 6- or 7-membered heterocyclic ring.

2. A photographic material according to claim 1, characterized in that R is a 5-(1-phenyl-tetrazolyl) group.

3. A photographic material according to claim 1, characterized in that Z represents the necessary atoms to close a 4-(1-phenyl-tetrazolyl-5-thione) group.

4. A photographic material according to claim 1, wherein an antifoggant precursor is used which corresponds with the formulae (II A) and (II B) characterized in that each of $Y^{10}$ and $Y^{20}$ represent a benzoyl group.

5. A photographic material according to claim 1, characterized in that the photographic material is for the production of dye images by image-wise transfer of a dye or dye precursor into a separate receiving material or into a receiving element forming together with the photographic material a mono-pack material.

6. A photographic material according to claim 5, characterized in that the mono-pack material includes a means for setting free an alkaline processing liquid the pH of which is above 11.5.

* * * * *